(12) United States Patent
Lee et al.

(10) Patent No.: US 10,150,973 B2
(45) Date of Patent: Dec. 11, 2018

(54) APPARATUS AND METHOD FOR SEPARATING AND REFINING PRODUCT MANUFACTURED BY MICROBIAL FERMENTATION BY USING ADSORBENT

(75) Inventors: Sang-Hyun Lee, Daejeon (KR); Moon-Ho Eom, Seoul (KR); Julia Lee, Daejeon (KR); Sang-Jun Jeon, Daejeon (KR); Jung-Hee Cho, Seongnam-si (KR); Jin Dal Rae Choi, Daejeon (KR)

(73) Assignee: GS CALTEX CORPORATION, Seoul (KR)

( * ) Notice: Subject to any disclaimer, the term of this patent is extended or adjusted under 35 U.S.C. 154(b) by 459 days.

(21) Appl. No.: 14/111,100

(22) PCT Filed: Apr. 13, 2012

(86) PCT No.: PCT/KR2012/002841
§ 371 (c)(1),
(2), (4) Date: Oct. 10, 2013

(87) PCT Pub. No.: WO2012/141542
PCT Pub. Date: Oct. 18, 2012

(65) Prior Publication Data
US 2014/0030777 A1    Jan. 30, 2014

(30) Foreign Application Priority Data

Apr. 14, 2011    (KR) ........................ 10-2011-0034883

(51) Int. Cl.
*C12P 7/16*    (2006.01)
*C12P 7/06*    (2006.01)
(Continued)

(52) U.S. Cl.
CPC .............. *C12P 7/06* (2013.01); *C12M 21/12* (2013.01); *C12M 23/58* (2013.01); *C12M 25/18* (2013.01);
(Continued)

(58) Field of Classification Search
CPC ...... C12M 21/12; C12M 23/58; C12M 25/18; C12M 25/20; C12M 47/10; C12M 47/12;
(Continued)

(56) References Cited

U.S. PATENT DOCUMENTS 1,315,585 A    9/1919    Weizmann
4,155,849 A *  5/1979    Baierl ................ B01D 53/0423
                                                            210/264
(Continued)

FOREIGN PATENT DOCUMENTS

CN    1403579 A  *  3/2003  ............ C12M 21/12
CN    1493694 A     5/2004
(Continued)

OTHER PUBLICATIONS

Mingbo Lu et al."CN 101914433A" English language translation. Translated on Jun. 18, 2015.*

(Continued)

*Primary Examiner* — Michael L Hobbs
*Assistant Examiner* — Liban M Hassan
(74) *Attorney, Agent, or Firm* — Hauptman Ham, LLP

(57) ABSTRACT

The present invention relates to an apparatus and a method for fermenting, separating, and refining a product, which is produced by cultivating a microorganism. The apparatus and the method for fermenting, separating, and refining, of the present invention, can separate and refine the product that is produced by microbial fermentation in a simple, continuous manner and with high efficiency.

7 Claims, 5 Drawing Sheets

(51) Int. Cl.
*C12M 1/00* (2006.01)
*C12M 1/12* (2006.01)
*C12P 7/28* (2006.01)
*B01D 15/08* (2006.01)
*B01D 15/18* (2006.01)

(52) U.S. Cl.
CPC ............ *C12M 25/20* (2013.01); *C12M 47/10* (2013.01); *C12M 47/12* (2013.01); *C12P 7/065* (2013.01); *C12P 7/16* (2013.01); *C12P 7/28* (2013.01); *B01D 15/08* (2013.01); *B01D 15/1885* (2013.01); *Y02E 50/10* (2013.01); *Y02E 50/17* (2013.01)

(58) Field of Classification Search
CPC ..... B01D 15/08; B01D 15/1885; Y02E 50/17; C12P 7/06; C12P 7/16; C12P 7/28; C12P 7/065
USPC .... 435/289.1, 132, 136, 148, 150, 160, 161, 435/283.1, 297.1
See application file for complete search history.

(56) References Cited

U.S. PATENT DOCUMENTS

| | | | |
|---|---|---|---|
| 4,520,104 A * | 5/1985 | Heady | C12P 7/16 435/160 |
| 4,946,582 A | 8/1990 | Torihata et al. | |
| 5,068,184 A * | 11/1991 | Knuth | A23L 1/23 426/650 |
| 6,114,577 A * | 9/2000 | Verhoff | C07C 51/47 210/177 |
| 2001/0021525 A1* | 9/2001 | Hirai | B01J 20/3242 435/283.1 |
| 2005/0245481 A1* | 11/2005 | Youn | C12P 19/60 514/54 |
| 2008/0015395 A1 | 1/2008 | D'Amore et al. | |
| 2009/0048103 A1 | 2/2009 | Suzuki et al. | |
| 2009/0101583 A1* | 4/2009 | Perry | B01D 61/58 210/664 |
| 2010/0252483 A1* | 10/2010 | Koseoglu | C10G 25/00 208/91 |

FOREIGN PATENT DOCUMENTS

| | | |
|---|---|---|
| CN | 101130791 A | 2/2008 |
| CN | 101386815 A | 3/2009 |
| CN | 101472859 A | 7/2009 |
| CN | 101914433 A | 12/2010 |
| EP | 0151470 A2 | 8/1985 |
| EP | 0458979 A1 * | 12/1991 ............ C12G 3/02 |
| JP | 02117388 A * | 5/1990 |
| JP | 2006333749 | 12/2006 |
| KR | 1020010046516 A | 6/2001 |
| WO | 8600339 A1 | 1/1986 |
| WO | 2008095896 A1 | 8/2008 |
| WO | 2009036076 A1 | 3/2009 |

OTHER PUBLICATIONS

Li et al., CN 1403579A, English language machine translation. Translated on Oct. 28, 2015.*
Mitsuda et al., JP-02117388A, English language human translation. Translation received on Oct. 8, 2015.*
Jianmin Xing, "English language machine translation of Chinese document CN 101386815B", translated on Jun. 2, 2016.*
Supplementary European Search Report dated Nov. 4, 2014.
Australian Office Action dated May 27, 2015 for Australian Patent Application No. 2012243504.
Chinese Office Action dated Jun. 9, 2014.
International Search Report for PCT/KR2012/002841, dated Nov. 30, 2012.
Durre, "An attractive biofuel", Biotechnol. J, 2:1525-1534, 2007.
Tsuchida et al., "Direct Synthesis of n-Butanol from Ethanol over Nonstoichiometric Hydroxyapatite", Ind. Eng. Chem. Res., 45: 8634, Oct. 31, 2006.
Mermelstein et al., "Metabolic Engineering of Clostridium acetobutylicum ATCC 824 for Increased Solvent Production by Enhancement of Acetone Formation Enzyme Activities Using a Synthetic Acetone Operon", Biotechnol. Bioeng., 42:1053, Nov. 5, 1993.
Nair et al., "Molecular Characterization of an Aldehyde/Alcohol Dehydrogenase Gene from Clostridium acetobutylicum ATCC 824", J. Bacteriol., 176:871, Feb. 1994.
Harris et al., "Characterization of Recombinant Strains of the Clostridium acetobutylicum Butyrate Kinase Inactivation Mutant: Need for New Phenomenological Models for Solventogenesis and Butanol Inhibition?", Biotechnol. Bioeng., 67:1, Jan. 5, 2000.
Ezeji et al., "Acetone butanol ethanol (ABE) production from concentrated substrate: reduction in substrate inhibition by fed-batch technique and product inhibition by gas stripping", Appl. Microbiol. Biotechnol., 63:653, 2004, Published Aug. 9, 2003.
Nielsen et al., "In Situ Product Recovery of n-Butanol Using Polymeric Resins", Bioeng. Biotech. 102:811-821, Sep. 2, 2008.
Chinese Office Action dated Nov. 10, 2015 in connection with the counterpart Chinese Patent Application No. 201280018471.4.
U.S. Final Office Action dated Oct. 9, 2015, in connection with the U.S. Appl. No. 14/111,425.
Thai Office Action dated May 2, 2018 in connection with the counterpart Thai Patent Application No. 1301005906.

* cited by examiner

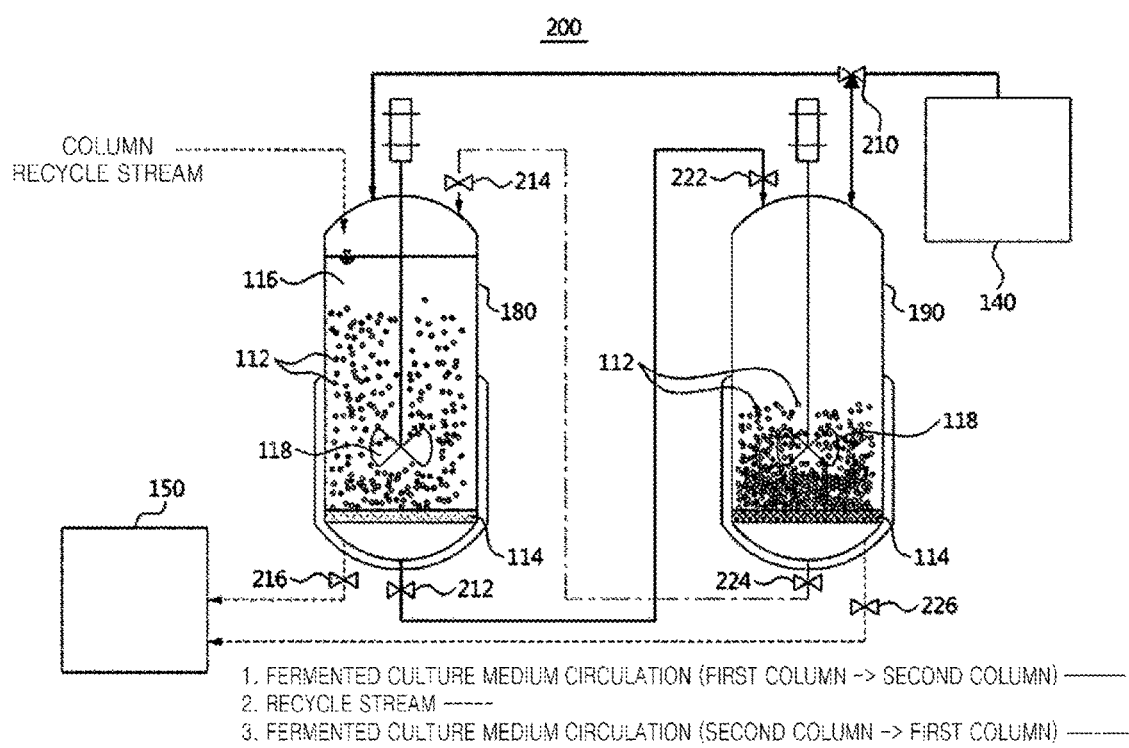

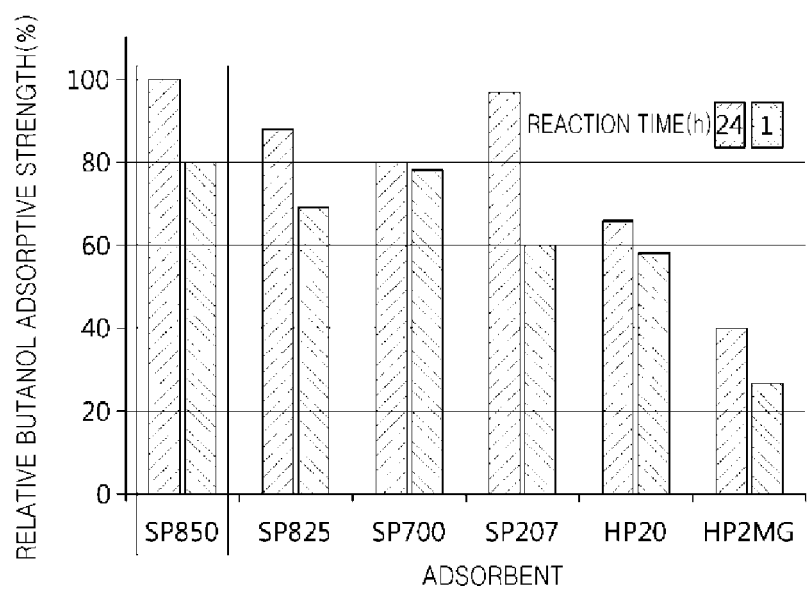
[FIG. 2]

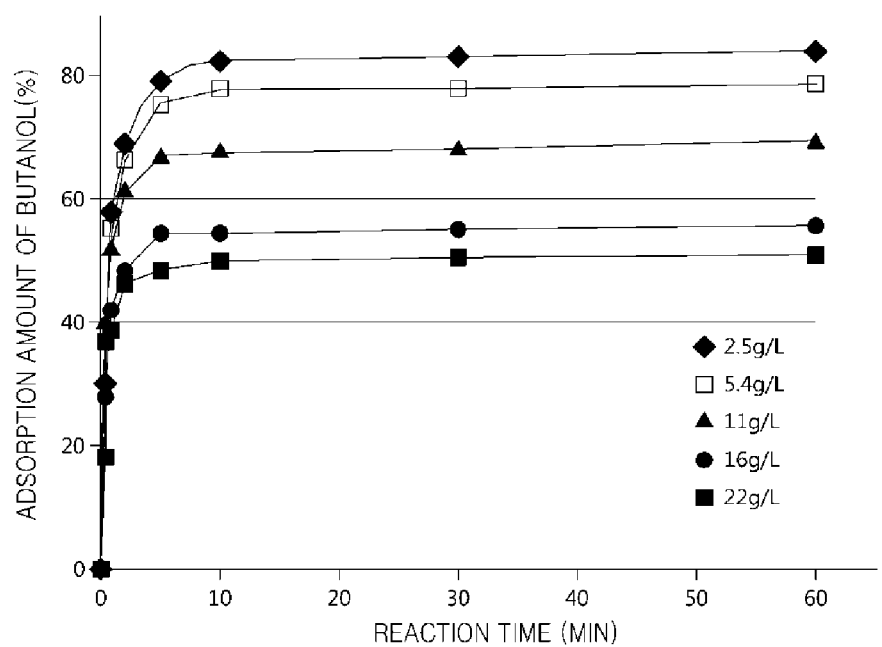
[FIG. 3]

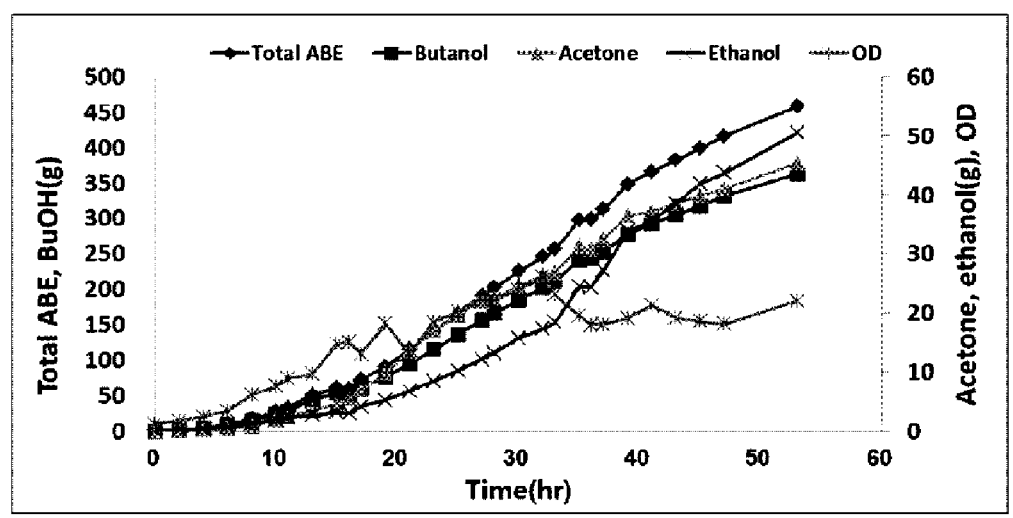
[FIG. 4]

[FIG. 5]
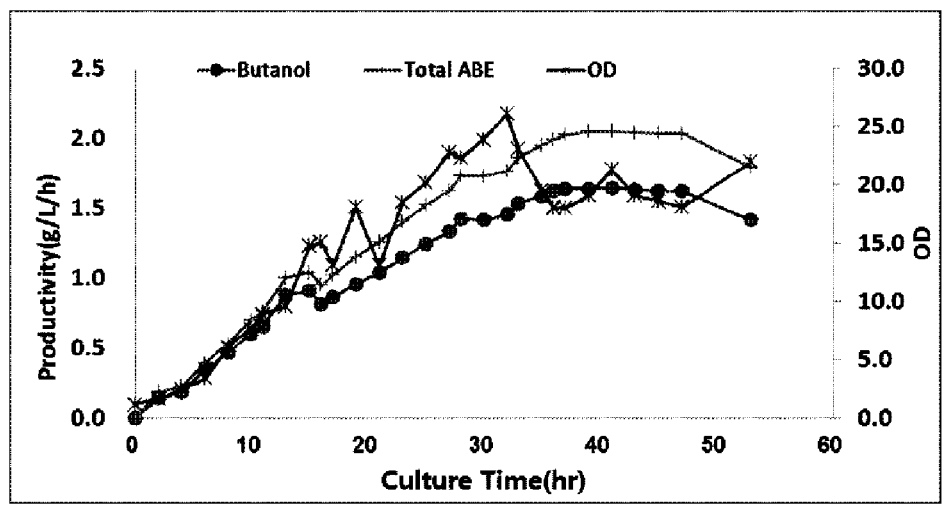
[FIG. 6]
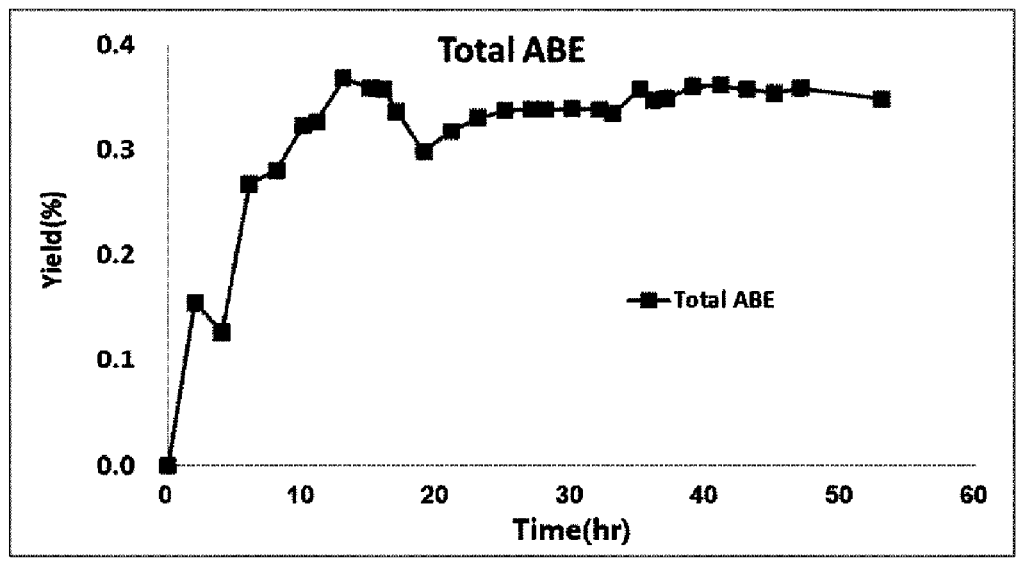

APPARATUS AND METHOD FOR SEPARATING AND REFINING PRODUCT MANUFACTURED BY MICROBIAL FERMENTATION BY USING ADSORBENT

CROSS REFERENCE TO RELATED APPLICATION

This application claims the priority of Korean Patent Application No. 10-2011-0034883, filed on Apr. 14, 2011 in the KIPO (Korean Intellectual Property Office). Further, this application is the National Phase application of International Application No. PCT/KR2012/002841 filed on Apr. 13, 2012, which designates the United States and was published in Korean.

TECHNICAL FIELD

The present invention relates to an apparatus and a method for continuously separating and refining products produced by microbial fermentation.

BACKGROUND ART

Butanol can be used as a chemical intermediate in cosmetics, perfume, hormone, a sanitizer, an industrial coating agent, a paint additive, fiber, a plastic monomer, medical supplies, vitamins, antibiotics, pesticides, or the like (Document [Durre, Biotechnol. J, 2:1525-1534, 2007]).

As the existing method for preparing butanol, a method of fermenting sugar using *Clostridium* strain to produce butanol, acetone, and ethanol (Document [U.S. Pat. No. 1,315,585]) has been used until the 1980s, but thereafter, an oxo process of synthesizing butanol from propylene obtained from petroleum has been widely used. However, since the method for preparing butanol based on petroleum is complicated due to using high temperature and high pressure and large amounts of hazardous wastes and carbon dioxide are discharged (Document [Tsuchida et al., Ind. Eng. Chem. Res., 45: 8634, 2006]). Recently, a demand for eco-friendly producing butanol from sustainable resources through microbial fermentation has been increased again.

However, as described above, currently, in most cases, butanol has been produced by a chemical synthesis method. An interest in research into biobutanol has been rapidly increased around the world due to an increase in oil price, environmental problems, and the like, but biobutanol has not yet been efficiently produced.

In the case of butanol, up to now, in most of the examples of producing butanol through fermentation, *Clostridium* strain is used. There is an example in which productivities of acetone, butanol, and ethanol were increased by 95%, 37%, and 90%, respectively, as compared to wild-type strains by inserting three genes, that is, acetoacetic acid decarboxylase (adc), CoA transferase A (ctfA), and CoA transferase B (cftB), into a vector and using a promoter of adc to thereby construct an artificial operon and then introducing this plasmid pFNK6 into *Clostridium acetobutylicum* ATCC 824 strains (Document [Mermelstein et al., Biotechnol. Bioeng., 42:1053, 1993]). In addition, there is an example in which the recombinant strain cloning and expressing alcohol/aldehyde dehydrogenase(aad) produced higher amount of butanol and ethanol than aceton when compared with wild type (Document [Nair et al., J. Bacteriol., 176:871, 1994]). Otherwise, as a method for inactivating a function of genes, there is an example of inactivating butyrate kinase (buk) and phosphotransacetylase (pta). It was reported that when a strain PJC4BK in which the buk gene was inactivated was fermented at pH of 5.0 or more, a production amount of butanol was significantly increased up to 16.7 g/L (Document [Harris et al., Biotechnol. Bioeng., 67:1, 2000]). However, it was reported that when the case of a strain in which a pta gene was inactivated was compared with the case of a wild-type strain, there was no significant difference in producing a solvent (Document [Harris et al., Biotechnol. Bioeng., 67:1, 2000]). In addition, it was reported that when fermentation was performed using a *Clostridium beijerinckii* BA101 strain, which is a mutant strain induced by random mutation, and maltodextrin as a carbon source, 18.6 g/L of butanol was produced (Document [Ezeji et al., Appl. Microbiol. Biotechnol., 63:653, 2004]). However, even in the case of using these recombinant strains, the production amount of butanol in a culture medium was significantly low (20 g/L or less) due to toxicity of butanol, which is a final product, such that it was impossible to industrially use these recombinant strains. Therefore, various method for extracting butanol in situ produced during a culture process to maintain a concentration of butanol in a culture medium at a level at which cytotoxicity is not generated have been developed. For example, it was reported that productivity may be increased by adsorbing butanol produced during continuous culture using activated carbon (Document [U.S. Pat. No. 4,520,104]).

However, in this method, only butanol is selectively adsorbed by the activated carbon and a concentration of the adsorbed butanol is low, such that it is difficult to recover butanol, and physical stability of activated carbon is insufficient, such that it is impossible to reuse the activated carbon. Therefore, there is a disadvantage in that extraction of butanol is expensive. An adsorption amount of butanol is in proportion to a concentration of butanol, but the concentration of butanol produced in continuous culture is low, such that the adsorption amount of butanol is also significantly low. Due to this problem, in spite of the continuous culture process, the productivity is not over 1 g/L/h. In addition, a column filled with the activated carbon may be physically clogged due to aggregation of cells, thereby causing a problem in a process. In this method, cell aggregates may clog the column and form a channel in a flow of the culture medium, such that it is difficult to allow the products such as butanol, acetone, isopropanol, ethanol, or the like, to be adsorbed in the entire adsorbent, thereby decreasing adsorption efficiency. A method of using an adsorbent except for activated carbon to increase productivity and a concentration of a solvent and using a recyclable adsorbent has been reported (Document [Nielsen et al., Bioeng. Biotech. 102:811-821, 2009]). The method is a method of adding the adsorbent in a culture medium and adsorbing butanol produced during a culture process in the adsorbent to recover butanol. According to this method, the adsorbent should be recovered from the culture medium, and essentially, a loss of the adsorbent is generated in a recovery process. In addition, impurities produced by microbes in the culture process and sugar, which is a raw material, are simultaneously adsorbed, such that purity and productivity of butanol are low at the time of recovering butanol. Further, an adsorption amount of butanol is in proportion to an amount of adsorbent added to the culture medium, but in this method, there is a limitation in an addition amount of the adsorbent in the culture medium. In addition, in this method, concentrations of ethanol and acetone are relatively high, which serves to desorb the adsorbed butanol, such that there is a limitation in increasing the concentration of butanol.

DISCLOSURE

Technical Problem

An object of the present invention is to provide a separation and refinement apparatus capable of continuously separating and refining products produced from a fermented culture medium of a microbe, and a separation and refinement method.

Technical Solution

In one general aspect, there is provided a continuous fermentation, separation, and refinement apparatus of products including:

a supply bath supplying a medium to a column;

at least two columns in which a microbe is cultured so as to produce the products and an adsorbent is filled; and at least one conversion part moving a culture medium in a first column to a second column when the products are sufficiently adsorbed in the first column to which the medium is supplied, stopping supply of the medium to the first column, and changing a flow of the medium so as to supply the medium to the second column.

In another general aspect, there is provided a continuous fermentation, separation, and refinement method of products including:

supplying a medium to a first column filled with an adsorbent;

culturing a microbe in the first column to produce the products; and moving a culture medium in the first column to a second column in the case in which the products are sufficiently adsorbed in the first column, stopping supply of the medium to the first column, and supplying the medium to the second column filled with the adsorbent.

Advantageous Effects

With the fermentation, separation, and refinement apparatus and method according to the present invention, the products produced by microbial fermentation may be simply and rapidly separated and purified.

DESCRIPTION OF DRAWINGS

FIG. 1 is a conceptual diagram showing a fermentation, separation, and refinement apparatus according to the present invention.

FIG. 2 is a comparison graph showing relative butanol adsorption performance of adsorbents.

FIG. 3 shows a kinetic analysis of butanol adsorption rate to the adsorbent with various concentrations.

FIG. 4 shows accumulated production amounts of the products according to the culture time.

FIG. 5 shows productivity of butanol and the entire products for each section according to the culture time.

FIG. 6 shows a yield change for each section according to the culture time.

BEST MODE

Advantages and features of the present invention and methods to achieve them will be elucidated from exemplary embodiments described below in detail with reference to the accompanying drawings. However, the present invention is not limited to the preferred embodiment disclosed herein but will be implemented in various forms. The preferred embodiments make the disclosure of the present invention thorough and are provided so that those skilled in the art can easily understand the scope of the present invention. Therefore, the present invention will be defined by the scope of the appended claims. Like reference numerals throughout the description denote like elements.

The present invention relates to a continuous fermentation, separation, and refinement apparatus of products including:

a supply bath supplying a medium to a column;

at least two columns in which a microbe is cultured so as to produce the products and an adsorbent is filled; and at least one conversion part moving a culture medium in a first column to a second column when the products are sufficiently adsorbed in the first column to which the medium is supplied, stopping supply of the medium to the first column, and changing a flow of the medium so as to supply the medium to the second column (FIG. 1).

In addition, the present invention relates to a continuous fermentation, separation, and refinement method of products including:

supplying a medium to a first column filled with an adsorbent;

culturing a microbe in the first column to produce the products; and moving a culture medium in the first column to a second column in the case in which the products are sufficiently adsorbed in the first column, stopping supply of the medium to the first column, and supplying the medium to the second column filled with the adsorbent.

In addition, the present invention relates to a continuous fermentation, separation, and refinement method of products including:

supplying a medium to a first column filled with an adsorbent;

culturing a microbe in the first column to produce the products;

moving a culture medium in the first column to a second column in the case in which the products are sufficiently adsorbed in the first column, stopping supply of the medium to the first column, and supplying the medium to the second column filled with the adsorbent; and desorbing the product from the adsorbent of the first column to which the supply of the medium is stopped to separate the product while fermentation proceeds in the second column to which the medium is supplied.

Hereinafter, the fermentation, separation, and refinement apparatus of products produced through microbial fermentation according to the present invention (hereinafter, referred to as the 'fermentation, separation, and refinement apparatus') and the fermentation, separation, and refinement method of products produced through microbial fermentation according to the present invention (hereinafter, referred to as the 'fermentation, separation, and refinement method') will be described in detail with reference to the accompanying drawings.

The fermentation, separation, and refinement apparatus according to the present invention includes at least two columns filled with the adsorbent. The fermentation, separation, and refinement apparatus according to the present invention includes, preferably, 2 to 20 columns filled with the adsorbent, more preferably, 2 to 10 columns, further more preferably, 2 to 5 columns, and most preferably, 2 to 3 columns. These columns may be represented by a first column, a second column, a third column, a fourth column, a fifth column, a sixth column, or the like. However, for convenience of explanation, hereinafter, the present invention will be described based on two columns. As used herein, the term "the first and second columns" means arbitrarily numbered columns for convenience of explanation, but does not means that the fermentation, separation, and refinement apparatus includes only two columns. In addition, according to the present invention, the culture medium is continuously supplied to several columns, such that a description of one column is similarly applied to other columns.

In a supply bath 140, the medium is supplied to the column, and a raw material is contained in the medium. As a result, the microbe is cultured in the column supplied with the medium, and the product is produced through microbial fermentation from the raw material.

An adsorbent 112 is filled in the first column, and a mixture in which the adsorbent 112 is mixed in the medium is formed by being supplied with the medium from the supply bath 140. Thereafter, the microbe, that is, an inoculum is inoculated and cultured in a first column 180. The product, which is a fermentation product, is produced by fermentation culture of the microbe, and at the same time the product is adsorbed in the adsorbent 112.

In this case, the fermentation, separation, and refinement apparatus according to the present invention may further include a stirrer 118 stirring the adsorbent and the product in the column. The medium and the adsorbent in the first column 180 are uniformly mixed with each other using the stirrer 118, thereby making it possible to prevent the medium, a culture medium, strains, and the adsorbent from being aggregated in the column, particularly, at a portion to which the medium is supplied, a portion at which a culture medium is discharged outside of the column, or the like. The culture medium of the microbe may circulate from an upper portion of the first column 180 to a lower portion thereof, but is not limited thereto.

In the case in which the product is sufficiently adsorbed in the first column, second and fifth conversion parts 212 and 222 are opened, such that the culture medium 116 in the first column 180 is moved to a second column 190. Therefore, the culture medium 116 in the first column 180 is supplied to the second column 190. At this time, since the second and fifth conversion parts 212 and 222 are opened, third and sixth conversion parts 214 and 224 are blocked, the culture medium 116 in the first column 180 may be introduced into the second column 190. At this time, a fourth conversion part 216 is opened, such that the product desorbed from the first column 180 may be introduced in a storage bath 150.

In addition, a first conversion part 210 blocks the direction of connection between the supply bath 140 and the first column 180, such that supply of the medium to the first column 180 is stopped. When the supply of the medium to the first column 180 is stopped, the first conversion part 210 is opened in a direction in which the supply bath 140 and the second column 190 are connected with each other. As a result, the medium is supplied from the supply bath 140 to the second column 190.

In the second column 190, fermentation is continuously performed by the microbe contained in the culture medium 116 introduced from the first column 180 using the medium and the raw material supplied from the supply bath 140. While the product is produced and adsorbed in the second column 190, a new medium may be continuously supplied from the supply bath 140. At this time, the culture medium 116 and the adsorbent 112 may be stirred in the second column 190 by the stirrer 118 so as to be uniformly mixed with each other.

That is, the product is sufficiently adsorbed, which means that since fermentation and culture of the microbe and production of the product are sufficiently performed in the first column, it is judged that the case of stopping production and separation of the product in the first column and culturing the microbe in the second column to produce the product is more preferable as compared to the case of continuously culturing the microbe in the first column to produce and adsorb the product. For example, butanol produced by the microbe is accumulated in a fermented culture medium of the microbe. When a concentration of butanol in the culture medium arrives at about 12 g/L, the microbe may be fatally affected by toxicity of butanol. Further, in the case in which an adsorption rate of the product with respect to the adsorbent is decreased or the case in which growth of the microbe in the column is inhibited by the product, or entire production efficiency is decreased, it is also advantageous that the fermentation and culture of the microbe in the first column is stopped, the culture medium is moved to the second column, and then culture is continuously performed in the second column. Therefore, in the case in which the product is sufficiently adsorbed may be a case in which the adsorption rate of the product with respect to the adsorbent is decreased, a case in which the growth of the microbe in the column is inhibited by an increase in the concentration of the product, a case in which productivity of the product of the microbe is decreased, or the like, and this case may be suitably determined by those skilled in the art according to the kind of microbe, the kind of adsorbent, the kind and composition of product, and the like.

Meanwhile, while culture proceeds in the second column to which the medium is supplied, desorption proceeds in the first column 180 to which supply of the medium is stopped. The term "desorption" means to elute the product adsorbed in the adsorbent from the adsorbent to allow the adsorbent to be recyclable.

The desorption may be performed using heat or an eluant, but is not limited thereto. In addition, a kind of means used in the desorption is not limited as long as it is suitable for a process condition. The desorption may be performed any time by using heat or the eluant, and a sufficiently large amount of product may be separated and purified with a small amount of adsorbent 112.

For example, desorption in the present invention may be performed by applying heat to the adsorbed product to vaporize the product. In this case, in view of cost, the heat may be preferably heat generated in a process, and the heat may be applied as steam, or hot air. The steam may be water in a vapor state and applied at a pressure of 0.01 to 6 bar. In addition, the hot air may be applied at a pressure of 0.01 to 6 bar and have a temperature at which the product may be eluted in a state in which the column and the adsorbent are not damaged. For example, the temperature of the hot air may be 100 to 200° C., preferable 110 to 150° C., more preferably 120 to 140° C., and most preferably 130° C. In addition, the desorption in the present invention may be performed using the eluant, and the eluant may be an organic solvent, or an acidic or basic aqueous solution. The organic solvent may be tetrahydrofuran, alcohol, ketone, ether, or ester, preferably, methanol, acetone, ethylacetate, diethylether, or methylethylketone, but is not limited thereto.

As an example of a desorption method, a tetrahydrofuran solvent is flowed into the column or water vapor is passed through the column. For example, desorption may be performed by flowing the tetrahydrofuran solvent having a double volume of a volume of the adsorbent at a flow rate of 10 mL/min or passing vapor preferably at 130° C. and 2 bar.

The desorption proceeds in a state in which the adsorbent in the first column 180 is not picked out, that is, an in-situ state. As described above, when the product is adsorbed in-situ in the adsorbent, butanol in the culture medium present in the first column 180 is maintained at a concentration at which butanol does not inhibit growth of the microbe or productivity of the product. While desorption proceeds in the first column 180, the medium is continuously supplied to the second column 190, and culture is continuously performed using the culture medium of the first column supplied from the first column 180. In addition, in the second column 190 to which the culture medium is supplied, adsorption continuously proceeds, such that production, separation, and refinement of the product may be continuously performed.

The fermentation, separation, and refinement apparatus according to the present invention may further include a filter 114 at an upper or lower portion of the column in order to prevent the adsorbent 112 from being eluted to thereby be lost.

Then, in the case in which the product is sufficiently adsorbed in the second column 190, the culture medium 116 in the second column 190 may be moved to a different column. The 'different column' may be the first column 180 or a third column. The 'different column' may be changed according to the number of columns included in the fermentation, separation, and refinement apparatus. That is, the number of columns in the fermentation, separation, and refinement apparatus is 3 or more, the 'different column' may be the third column, and the culture medium 116 in the second column 190 is moved to the third column.

In the case in which the number of columns in the fermentation, separation, and refinement apparatus is 2, the 'different column' is the first column 180, and the first column 180 is in a state in which desorption is completed while adsorption of the product in the second column 120 is performed. In this case, the third and sixth conversion parts 214 and 224 are opened, such that the culture medium 116 in the second column 190 is moved to the first column 180. Next, the first conversion part 210 blocks the direction of connection between the supply bath 140 and the second column 190, such that supply of the medium to the second column 190 is stopped.

Thereafter, desorption in the second column 190 proceeds, and at this time, a seventh conversion part 226 is opened, such that the desorbed product may be introduced in the storage bath 150. The product desorbed from the filter is introduced and stored in the storage bath 150. Meanwhile, fermentation and culture of the microbe, production of the product, and adsorption of the produced product are continuously performed in the different column to which the culture medium 116 of the second column 190 is supplied.

The culture medium 116 may circulate between the columns in the fermentation, separation, and refinement apparatus according to the present invention by repeating the above-mentioned processes, the adsorbent in the columns may be reused, and the product may be continuously produced, separated, and purified.

Hereinabove, the fermentation, separation, and refinement apparatus and method of the present invention are briefly described. Hereinafter, the present invention will be described in detail.

The fermentation, separation, and refinement apparatus and method according to the present invention may simply and continuously separate and purify the product produced by culturing the microbe, and since desorption may be suitably performed, adsorption efficiency may also be high. Therefore, the fermentation, separation, and refinement apparatus and method according to the present invention may separate and purify the product produced by culturing the microbe with the high efficiency.

As the microbe of the present invention, any microbe may be used as long as the microbe may produce the product, which is a biofuel, from the raw material, but the present invention is not particularly limited. For example, the microbe of the present invention may be bacteria, yeast, fungus, or the like, and preferably, bacteria or yeast. The microbe of the present invention may be a wild-type microbe or genetically modified microbe. Preferably, the microbe of the present invention may be a wild type strain of *Clostridium* genus, *E. coli*, or the like, or a strain of which genes are recombined so as to increase productivity of a specific product, but it is obvious to those skilled in the art that the present invention is not limited thereto.

For example, in the case of using bacteria in the *Clostridium* genus of which buk gene coding butyrate kinase is deleted as the microbe of the present invention, there is an advantage in that products such as butanol, acetone, isopropanol, ethanol, or the like, may be produced at a high concentration under anaerobic conditions while not producing a large amount of butyric acid. For example, in the case of using bacteria in the *Clostridium* genus of which buk gene coding the butyrate kinase, pta gene coding phosphotransacetylase, and ackA gene coding acetate kinase are deleted as the microbe of the present invention, there is an advantage in that products such as butanol, acetone, isopropanol, ethanol, or the like, may be produced at a high concentration under anaerobic conditions while not producing large amounts of other organic acids. In addition, in the case of using bacteria in the *Clostridium* genus of which adc gene coding acetoacetic acid decarboxylase is deleted as the microbe of the present invention, there is an advantage in that butanol may be selectively produced at a high concentration while not producing acetone. Further, in the case of using bacteria in the *Clostridium* genus transformed with a plasmid including genes coding secondary alcohol dehydrogenase (ald), which is an enzyme converting acetone into isopropylalcohol, there is an advantage in that high value-added products such as butanol, isopropanol, ethanol, or the like, may be produced.

The gene modified *Clostridium* may be constructed by a method disclosed in the released paper (Document [Microbiology (1996), 142, 2079-2086]). For example, PJC4BK or BKM19 (KCTC 10558BP), which is a mutant strain, may be prepared by deleting the butyrate kinase gene (buk) in *Clostridium acetobutylicum*. Thereafter, mutant strains may be prepared by deleting the phosphotransacetylase gene (pta) and the acetate kinase gene (ackA) from the strain, respectively. Next, it may be confirmed that when these strains are cultured under anaerobic conditions, the products such as butanol, acetone, isopropanol, ethanol, or the like, are produced at a high concentration.

The microbe of the present invention may be cultured by a fed-batch culture method or continuous culture method. The continuous culture method is a method of supplying a fresh medium to a culture bath at a predetermined rate and simultaneously discharging the same amount of fermented culture medium of the microbe to thereby always maintain the culture medium to be constant in the culture bath.

Meanwhile, the fed-batch culture method, which is a culture method of intermittently supplying a medium, is a method of optionally controlling a concentration of a substrate in the culture medium.

The raw material of the present invention may be a material capable of being used by the microbe at the time of fermentation to thereby produce the product, and a kind thereof is not particularly limited. For example, the raw material of the present invention may be biomass, sugars, fatty acids, or the like. The biomass may be a woody biomass, grains, or the like, but is not limited thereto. The sugars may be monosaccharides, polysaccharides, polysaccharides, or the like, be (C3-C12) sugar, and include polysaccharides produced during a hydrolysis process of the biomass. For example, the sugars may be glycerol, glucose, sucrose, xylose, starch, cellulose, or the like, but is not limited thereto. The fatty acid may be (C2-C24)fatty acid, for example, acetic acid, butyric acid, propionic acid, or the like, but is not limited thereto.

The product of the present invention is a fermented product produced by the microbe. Preferably, the product of the present invention may be alcohol, ketone, ester, carboxylic acid, or the like, as a biofuel, but is not limited thereto. For example, the alcohol may be (C2-C6)alcohol, preferably alcohol having at most 4 carbon atoms, more preferably, ethanol, propanol, isopropanol (2-propanol), 1,2-propanediol, 1,3-propanediol, 1,3-butanediol, 1,4-butanediol, butanol, or the like, but is not limited thereto. The ketone may be (C3-C8)ketone. For example, the ketone may be acetoacetate, acetone, or the like, but is not limited thereto. The ester may be (C4-C8)ester, for example, ethyl acetate, ethyl butyrate, butyl acetate, butyl butyrate, or the like, but is not limited thereto. The carboxylic acid may be (C2-C8)carboxylic acid, for example, acetic acid, butyric acid, propionic acid, or the like, but is not limited thereto. Preferably, the product of the present invention may be butanol, isopropanol, ethanol, or acetone, but is not limited thereto.

The adsorbent 112 of the present invention may be filled at a volume fraction of 0.1 to 99% based on a capacity, that is, a volume of the column containing the adsorbent 112. In the case in which the volume fraction of the adsorbent is less than 0.1 volume % based on the volume of the column, the amount of the adsorbent 112 is insufficient, such that adsorption may not be suitably performed. Further, in the case in which the volume fraction of the adsorbent is 99 volume % or more, aggregates of the adsorbent 112 or cells are formed in the column, such that adsorption may not be suitably performed.

A type of column to which the culture medium is supplied may be a slurry reactor type, a fluidized reactor type, or a packed reactor type. The fluidized reactor type column is a column containing a small amount of an adsorbent and having high fluidity, the slurry reactor type column is a column containing an adsorbent suspended in a culture medium, and the packed reactor type column is a column in which an adsorbent is substantially packed. In this case, intermediate type columns of the three type columns may be divided into the three type columns depending on which column they are close to, and although the inside of the column is the intermediate type of the three types, the column may be included in any one of the three types. For example, according to the degree of fluidity, when it is judged that the adsorbent is packed so as not to substantially flow, the column may be classified as the packed type column, and when it is judged that the adsorbent may be suspended, the column may be classified as the slurry reactor type column.

The conversion part of the present invention serves to change and control a flow of the medium or the culture medium 116 and may control so that the medium is supplied from the supply bath 140 to a specific column or send the culture medium discharged from a specific column to the another column. A single or a plurality of conversion parts may be used, and the conversion part may be suitably installed by those skilled in the art according to the design of the fermentation, separation, and refinement apparatus of the present invention.

Experimental Example 1

In order to select a suitable adsorbent used in the Example of the present invention, butanol adsorption performance of various adsorbents prepared by Mitsubishi Corp. was compared. After various kinds of adsorbents were added to 50 mL of a phosphate buffer solution (50 mM) containing 2% butanol and left for 1 hour while being stirred, a concentration of butanol remaining the solution was analyzed using gas chromatography. As a result, it was analyzed that the adsorbent SP850 had most excellent performance (FIG. 2), but the kind of adsorbent is not limited to SP850. Analysis of products such as butanol, acetone, isopropanol, ethanol, or the like, was performed using the gas chromatography (Agilent, USA), and analysis conditions were as shown in the following Table 1.

TABLE 1

| Gas chromatography analysis condition | |
|---|---|
| Injector temperature | 320° C. |
| Detectortemperature | 320° C. |
| Injector split ratio | 20/1 |
| Injection volume | 0.1 μL |
| Oven conditions | 80° C./20 min |
| Air flux | 300 mL/min |
| H2 flux | 30 mL/min |
| Column: Supelco CarboWAX | |

Experimental Example 2

In order to confirm an adsorption rate of butanol adsorbed in the adsorbent SP850, kinetic analysis was performed on adsorption of butanol. In the culturing used in the Example of the present invention, since butanol should be adsorbed for a short time for which the culture medium passed through the column, the adsorption rate of butanol was significantly important. First, 3 g (dried weight) of the adsorbent was added to 50 mL of liquid *Clostridium* growth media (CGM) in which butanol was contained at various concentrations, and sampling was performed at sample times of 30 seconds, 1 minute, 2 minutes, 5 minutes, 10 minutes, 30 minutes, and 1 hour while stirring the mixture at 200 rpm. Then, a concentration of butanol remaining the solution was confirmed through gas chromatography analysis.

As a result, it may be confirmed that butanol was adsorbed within about 1 minute in various concentration ranges (FIG. 3).

Experimental Example 3

In order to confirm an amount of adsorbent suitable for fed-batch fermentation and fermentation conditions, a recombinant *Clostridium* strain was constructed. A recombinant *Clostridium* strain (*C. acetobutylicum* PJC4BK- IPA2) containing secondary alcohol dehydrogenase required for microbial fermentation was constructed. The Clostridium strain was cultured in 60 mL of liquid Clostridium growth media (CGM, 0.75 g/L K2HPO4, 0.75 g/L KH2PO4, 0.7 g/L, MgSO4H2O, 0.017 g/L MnSO4H2O, 0.01 g/L, FeSO4H2O, 2 g/L (NH4)2SO4, 1 g/L NaCl, 2 g/L asparagine, 0.004 g/L p-aminobenzoic acid, 5 g/L yeast extract, 4.08 g/L CH3COONaH2O, and 80 g/L glucose) under anaerobic conditions until OD600 reached 0.5. Then, the culture medium was left in ice water for 10 minutes, and the culture medium was centrifuged with 7000 G at 4° C. for 10 minutes. 15 mL of sucrose (270 mM) and 0.11 mL of NaH2PO4 (686 mM, pH 7.4) were mixed with each other, thereby preparing an electroporation buffer solution. After a cell pellet was washed with the electroporation buffer solution prepared as described above three times, the washed cell pellet was suspended in 2 mL of the same buffer solution, thereby constructing recombinant cells. 0.5 to 2.0 μg g of plasmid containing secondary alcohol dehydrogenase gene was added to the prepared cells (500 μl) for transformation, and then electroporation (4 mm cuvette, 2.5 kV, ∞Ω, 25 uF) was performed using Gene pulser II (Bio-Rad Corp.), followed by anaerobic culture in the culture medium to which antibiotic was added, thereby completing the construction of recombinant strain. All of the plasmids used for transformation were constructed so as not to be affected by restriction system of the Clostridium strain by being methylated in E. coli ER2275 transformed with a pAN1 vector before electroporation.

The Clostridium strain PJC4BK-IPA2 cultured as described above was smeared on a CGM/chlorampenicol plate medium and anaerobically cultured overnight at 37° C. 2 cultured colonies were inoculated in a 50 mL disposable tube in which 20 mL of CGM/chlorampenicol culture medium was contained and anaerobically cultured while being placed at 37° C. until OD600 reached 3. The culture broth was inoculated again in a liquid CGM containing 100 mL of 8% glucose and anaerobically cultured while being placed at 37° C. until OD600 reached 2 to 3. Then, the resultant was inoculated in a culture bath in which 1 L of the liquid CGM and 0 mL (0 g/L, dried weight), 200 mL (60 g/L), 250 mL (75 g/L), 300 mL (90 g/L), 350 (105 g/L), and 400 mL (120 g/L) of the adsorbent were contained, respectively, and cultured. After starting culture, concentrations of the produced butanol, acetone, isopropanol, ethanol, or the like, were analyzed per 3 hours while maintaining a concentration of glucose at 20 g/L or more. Analysis of products such as butanol, acetone, isopropanol, ethanol, or the like, was performed using the gas chromatography (Agilent, USA), and analysis conditions were the same as those shown in Table 1.

Concentrations of sugar and organic acid may be confirmed using high pressure liquid chromatography (HPLC), gas chromatography, and a sugar analyzer after centrifuging the culture medium and obtaining a supernatant. Conditions of the HPLC were as follows: water containing 0.01N sulfuric acid was used as a mobile phase, and a flow rate was 0.6 mL/min. As the column, Aminex87H and Aminex87P (Bio-rad, USA) were used, and the produced sugar and organic acid were analyzed using a reflective index (RI) detector.

As a result, it may be confirmed that the recombinant and mutant strains cultured as described above produced larger amounts of products such as butanol, acetone, isopropanol, ethanol, or the like in the culture medium containing the adsorbent, and the optimal amount of the adsorbent was 250 mL/L as shown in Table 2.

TABLE 2

| Amount of adsorbent (mL/L) | product (g/L) | | | | | Yield (%) | Production rate (g/L/h) | Consumption amount of glucose (g/L) |
| | Acetone | Ethanol | Butanol | IPA | Sum | | | |
| --- | --- | --- | --- | --- | --- | --- | --- | --- |
| 0 | 0.4 | 4.1 | 16.8 | 3.3 | 25 | 35 | 0.6 | 70 |
| 200 | 0.6 | 7.7 | 23.1 | 9.6 | 40 | 33 | 1.35 | 120 |
| 250 | 3.6 | 8.4 | 27.6 | 6.2 | 46 | 34 | 1.2 | 132 |
| 300 | 2.3 | 6.2 | 27.1 | 7.8 | 43.3 | 30 | 1.09 | 153 |
| 350 | 7.0 | 7.2 | 25.1 | 5.4 | 44.7 | 28 | 1.06 | 161 |
| 400 | 6.4 | 8.53 | 27.2 | 7.6 | 49.7 | 30 | 1.10 | 166 |

Experimental Example 4

The same culture medium, culture method, and analysis method as in the Experimental Examples were used, and 200 mL of the adsorbent was used, such that reusability of the adsorbent was tested. After the culture was completed, the products such as butanol, acetone, isobutanol, or ethanol, adsorbed in the adsorbent were recovered using a column for desorption and eluted by flowing a tetrahydrofuran solvent having a double volume of a volume of the adsorbent at a flow rate of 10 mL/min. Then, the total amount of products was analyzed using gas chromatography, and the total amount of adsorbed products was compared thereto every time, thereby analyzing performance of the adsorbent.

As a result, it was confirmed that even though the adsorbent was reused, adsorption of the product was suitably performed (Table 3).

TABLE 3

| The number of reuse | Product (g/L) | | | | | Yield (%) | Production rate (g/L/h) | Culture time (h) | Consumption amount of glucose (g/L) |
| | Acetone | Ethanol | Butanol | IPA | Sum | | | | |
| --- | --- | --- | --- | --- | --- | --- | --- | --- | --- |
| 1 | 2.2 | 6.6 | 26.9 | 6.6 | 42 | 36 | 1.02 | 41 | 117 |
| 2 | 1.8 | 6.4 | 20.0 | 7.7 | 36 | 35 | 1.20 | 30 | 104 |
| 3 | 0.6 | 7.7 | 23.1 | 9.6 | 40 | 33 | 1.35 | 30 | 120 |

TABLE 3-continued

| The number of reuse | Product (g/L) | | | | | Yield (%) | Production rate (g/L/h) | Culture time (h) | Consumption amount of glucose (g/L) |
| --- | --- | --- | --- | --- | --- | --- | --- | --- | --- |
| | Acetone | Ethanol | Butanol | IPA | Sum | | | | |
| 4 | 1.8 | 7.1 | 23.2 | 7.6 | 40 | 33 | 1.32 | 30 | 121 |
| 5 | 1.7 | 4.7 | 23.4 | 6.5 | 37 | 34 | 1.23 | 30 | 110 |
| 6 | 1.5 | 7.3 | 22.9 | 9.0 | 41 | 37 | 1.03 | 40 | 110 |
| 7 | 1.4 | 6.9 | 22.3 | 8.5 | 39 | 33 | 1.02 | 39 | 118 |
| 8 | 3.3 | 5.6 | 21.4 | 5.5 | 36 | 32 | 1.00 | 36 | 110 |
| 9 | 1.5 | 6.7 | 20.9 | 7.1 | 36 | 32 | 1.01 | 36 | 112 |
| 10 | 2.1 | 6.3 | 22.9 | 6.5 | 38 | 36 | 1.26 | 36 | 104 |

<Experimental Example 5> Preparation of Products Such as Butanol, Acetone, Isopropanol, Ethanol, and the Like, Using Fed-Batch Culture Method Based on the results optimized in the Experimental Examples, products such as butanol, acetone, isopropanol, ethanol, and the like, were prepared using a fed-batch culture method. Experimental methods and analysis were performed similarly to those in <Example 3>, but fermentation of glucose contained in the culture medium was performed in a state in which the concentration of the CGM culture medium containing 250 mL of the adsorbent was the same or increased 2 times as compared to <Experimental Example 3>, respectively, such that amounts of the prepared products such as butanol, acetone, isopropanol, ethanol, and the like, were compared with each other.

As a result, it may be confirmed that the recombinant and mutant strains cultured as described above produced larger amounts of butanol, acetone, isopropanol, ethanol, and the like, during the culture process, depending on an amount of a nutrient, as shown in Table 4. This result means that in the case of simultaneously injecting the nutrient and carbon source according to the culture method in Example of the present invention, the high concentration products such as butanol, acetone, isopropanol, ethanol, and the like, may be synthesized with a high yield in the continuous culture as well as the fed-batch culture.

pump was mounted so as to circulate a culture medium in the column. 4-way valves were mounted at an inlet and an outlet of the column so as to flow an eluant when the products such as butanol, acetone, isopropanol, ethanol, and the like, were sufficiently adsorbed in the adsorbent in the column during the culture process to thereby perform desorption in real time. When the products were sufficiently adsorbed in the first column, the culture medium was moved to the second column by adjusting the valve. Products that were not yet adsorbed in the adsorbent were contained in the culture medium discharged from the column. In the first column in which the culture medium was moved to the second column, the products were desorbed in a state in which the adsorbent in the first column was not picked out. While desorption proceeded in the first column, sugar and nutrients were continuously supplied from a supply bath 140 to the second column to which the moved culture medium was supplied, and production of the products by the microbe and adsorption of the produced product proceeded.

Thereafter, similarly, when the products were sufficiently adsorbed in the second column, the culture medium was moved to the first column by adjusting the valve. The adsorbent in the first and second columns may be reused by repeating the above-mentioned processes. A circulation direction of the culture medium is a direction from the upper portion of the column to the lower portion thereof, but the circulation direction did not matter.

TABLE 4

| Culture condition | | Product (g/L) | | | | | Solvent increase rate (%) | Yield (%) | Production rate (g/L/h) |
| --- | --- | --- | --- | --- | --- | --- | --- | --- | --- |
| adsorbent | Concentration of CGM | Acetone | Ethanol | Butanol | IPA | Sum | | | |
| ○ | 2 | 0.77 | 9.70 | 32.4 | 9.06 | 52 | 108 | 33 | 1.24 |
| ○ | 1 | 3.63 | 8.4 | 27.6 | 6.2 | 46 | 84 | 35 | 1.21 |
| X | 1 | 0.43 | 4.1 | 16.8 | 3.3 | 25 | 0 | 35 | 0.6 |

<Experimental Example 6> Manufacturing of Fed-Batch Culture Apparatus and Preparation of Products Such as Butanol, Acetone, Isopropanol, Ethanol, and the Like, Using Culture Method The fed-batch culture apparatus shown in FIG. 1 was manufactured. In this case, two columns were included therein. In order to prevent the adsorbent from being eluted at an upper or lower portion of the column having a volume of 5 L to thereby be lost, a filter (about 150 μm) was mounted, and then a stirrer was mounted. Thereafter, 400 mL of adsorbent SP850 was filled in two columns (referred to as first and second columns, respectively). These columns were connected to a culture bath using a silicon tube, and a Meanwhile, in the fermentation, separation, and refinement apparatus according to the embodiment of the present invention, C. acetobutylicum PJC4BK strains capable of producing butanol, acetone, isopropanol, ethanol, and the like, were cultured using a fed-batch culture apparatus. First, 800 mL of seed culture was performed overnight in CGM medium and the seed culture was inoculated into a reactor in which 3.2 L of the liquid CGM was contained. In Experimental Examples of the present invention, the spawn was cultured by general batch fermentation, but in order to prepare the high concentration products such as butanol, acetone, isopropanol, ethanol, and the like, at a higher cell concentration, cell immobilization type culture may be performed.

After starting the culture, when the products were sufficiently adsorbed in the adsorbent of the first column, the culture medium containing the products were moved to the second column through the pump at a flow rate of 150 mL/min. It was confirmed that the adsorbent SP850 was suspended in the culture medium while the culture medium passed through the filter of the first column to form a slurry phase, such that the flow of the culture medium was not blocked by the aggregates of cells, and the culture medium passed through the first column. In addition, a sample of the culture medium of the first column was taken per about 2 hours, and concentrations of butanol, acetone, isopropanol, ethanol, and the like, were analyzed using gas chromatography. During the culture process, the concentration of the sugar in the culture medium was maintained at 20 g/L by supplying the liquid CGM containing 20% glucose to the culture bath, and in order to maintain the volume of the culture medium at 4 L, some of the culture medium and the product were continuously removed. Amounts of the products such as butanol, acetone, isopropanol, ethanol, and the like, were confirmed through gas chromatography.

As a result, the fed-batch culture was stably performed for about 53 hours as shown in FIGS. 4 to 6 (ABE: acetone, butanol, and ethanol). It may be confirmed that when the product started to be adsorbed in the adsorbent in the first column to thereby be sufficiently adsorbed in the first column, the culture medium was moved and supplied to the second column, and the product was continuously produced and adsorbed in the adsorbent of the second column, such that the products such as butanol, acetone, isopropanol, ethanol, and the like, were always maintained at a low concentration in the culture medium. In addition, it was confirmed that since the product was adsorbed in the adsorbent to thereby be maintained at a low concentration in the column, the microbe was not affected by toxicity of butanol, thereby making it possible to stably prepare the product while maintaining a constant cell density (OD).

The products such as butanol, acetone, isopropanol, ethanol, and the like, adsorbed in the first column were desorbed using water vapor (130° C.). As a result, it was confirmed that the products such as butanol, acetone, isopropanol, ethanol, and the like, were excellently adsorbed and desorbed. Further, it was confirmed that even in the case of repeating replacement of the column 20 times or more, the adsorption performance of the column was not significantly decreased (Tables 5 and 6).

TABLE 5

|  | Product (g) | | | | Yield (%) | Production rate (g/L/h) | Culture time (hour) | Consumption amount of glucose (g) |
| --- | --- | --- | --- | --- | --- | --- | --- | --- |
|  | Acetone | Ethanol | Butanol | Sum | | | | |
| Final culture medium | 9.8 | 20.3 | 42.4 | 72.3 | 31 | 2.06 | 53 | 1478 |
| Desorption solution | 27.9 | 20.2 | 292.5 | 340.7 | | | | |
| Removed culture medium | 7.6 | 9.9 | 27.3 | 44.9 | | | | |
| Sum | 45.3 | 50.5 | 362.3 | 458.0 | | | | |

TABLE 6

| A | B | C | OD | D | Concentration in culture medium(g/L) | | | | | Desorption(g) | | | |
| --- | --- | --- | --- | --- | --- | --- | --- | --- | --- | --- | --- | --- | --- |
| | | | | | Glucose | Acetone | EtOH | BuOH | ABE | Acetone | EtOH | BuOH | ABE |
|  | 1 | 0 | 1.2 | 4.0 | 77.6 | 0.0 | 0.0 | 0.0 | 0.1 | | | | |
|  | 1 | 13 | 9.6 | 3.9 | 42.4 | 0.8 | 0.7 | 5.8 | 7.3 | | | | |
|  | 1 | 15 | 14.8 | 3.9 | 34.4 | 1.0 | 0.8 | 7.8 | 9.6 | | | | |
| 1 | 1 | 16 | 15.1 | 3.9 | 30.6 | 1.2 | 0.6 | 8.7 | 10.5 | 0.7 | 0.2 | 17.6 | 18.5 |
| 2 | 2 | 17 | 13.1 | 4.2 | 31.4 | 1.3 | 0.9 | 7.2 | 9.3 | 0.9 | 0.3 | 16.2 | 17.4 |
| 3 | 1 | 19 | 18.1 | 4.2 | 17.8 | 1.7 | 1.0 | 6.7 | 9.4 | 1.1 | 0.3 | 15.0 | 16.4 |
| 4 | 2 | 21 | 13.1 | 4.3 | 20.4 | 2.0 | 1.2 | 6.9 | 10.1 | 1.4 | 0.4 | 15.8 | 17.6 |
| 5 | 1 | 23 | 18.5 | 4.3 | 21.6 | 2.4 | 1.4 | 7.4 | 11.2 | 1.4 | 0.5 | 15.7 | 17.6 |
| 6 | 2 | 25 | 20.2 | 4.3 | 22.0 | 2.4 | 1.5 | 7.8 | 11.8 | 1.7 | 0.6 | 17.7 | 19.9 |
| 7 | 1 | 27 | 22.8 | 4.3 | 20.6 | 2.4 | 1.8 | 8.2 | 12.4 | 1.5 | 0.5 | 16.7 | 18.8 |
| 8 | 2 | 28 | 22.3 | 4.2 | 20.6 | 2.3 | 1.8 | 7.3 | 11.4 | 1.6 | 0.8 | 15.6 | 17.9 |
| 9 | 1 | 30 | 23.9 | 4.3 | 20.8 | 2.2 | 2.1 | 7.8 | 12.2 | 1.3 | 0.7 | 13.1 | 15.1 |
| 10 | 2 | 32 | 26.1 | 4.3 | 22.0 | 2.1 | 2.2 | 8.1 | 12.5 | 1.4 | 0.8 | 15.0 | 17.2 |
| 11 | 1 | 33 | 23.1 | 4.2 | 20.6 | 2.0 | 2.2 | 7.1 | 11.3 | 1.3 | 0.9 | 13.3 | 15.5 |
| 12 | 2 | 35 | 19.5 | 4.3 | 21.6 | 2.4 | 3.0 | 9.4 | 14.8 | 1.3 | 0.9 | 14.2 | 16.5 |
| 13 | 1 | 36 | 18.0 | 4.2 | 22.2 | 2.0 | 2.8 | 7.6 | 12.4 | 2.1 | 1.9 | 13.0 | 17.0 |
| 14 | 2 | 37 | 18.0 | 4.2 | 22.2 | 1.9 | 2.9 | 7.1 | 11.9 | 1.8 | 1.9 | 12.1 | 15.8 |
| 15 | 1 | 39 | 19.1 | 4.3 | 21.4 | 2.0 | 3.4 | 8.0 | 13.4 | 1.9 | 2.1 | 13.1 | 17.1 |
| 16 | 2 | 41 | 21.3 | 4.3 | 26.0 | 2.0 | 3.6 | 7.8 | 13.3 | 1.3 | 1.3 | 16.7 | 19.3 |
| 17 | 1 | 43 | 19.1 | 4.3 | 28.8 | 1.7 | 3.4 | 5.8 | 10.9 | 1.3 | 1.4 | 14.0 | 16.7 |
| 18 | 2 | 45 | 18.6 | 4.3 | 30.8 | 1.8 | 3.9 | 5.8 | 11.5 | 1.2 | 1.3 | 13.1 | 15.6 |
| 19 | 1 | 47 | 18.1 | 4.3 | 38.8 | 1.6 | 3.7 | 6.2 | 11.6 | 1.5 | 1.9 | 12.7 | 16.1 |
| 20 | 2 | 53 | 22.0 | 4.8 | 39.0 | 2.0 | 4.2 | 8.9 | 15.1 | 1.2 | 1.3 | 12.1 | 14.7 |

TABLE 6-continued

| | | | | | Discharge amount of solvent(g) | | | | Total accumulated amount of solvent(g) | | | |
|---|---|---|---|---|---|---|---|---|---|---|---|---|
| A | B | C | OD | D | Acetone | EtOH | BuOH | ABE | Acetone | EtOH | BuOH | ABE |
| | 1 | 0 | 1.2 | 4.0 | | | | | 0.1 | 0.1 | 0.0 | 0.2 |
| | 1 | 13 | 9.6 | 3.9 | | | | | 3.4 | 2.7 | 45.0 | 51.1 |
| | 1 | 15 | 14.8 | 3.9 | | | | | 4.6 | 3.1 | 53.4 | 61.1 |
| 1 | 1 | 16 | 15.1 | 3.9 | 0.0 | 0.0 | 0.3 | 0.4 | 5.4 | 3.0 | 50.8 | 59.2 |
| 2 | 2 | 17 | 13.1 | 4.2 | 0.0 | 0.0 | 0.1 | 0.1 | 7.0 | 4.1 | 61.4 | 72.6 |
| 3 | 1 | 19 | 18.1 | 4.2 | 0.0 | 0.0 | 0.1 | 0.2 | 9.9 | 5.3 | 76.0 | 91.1 |
| 4 | 2 | 21 | 13.1 | 4.3 | 0.4 | 0.2 | 1.3 | 1.9 | 13.5 | 6.8 | 94.9 | 115.1 |
| 5 | 1 | 23 | 18.5 | 4.3 | 0.6 | 0.4 | 1.6 | 2.6 | 17.0 | 8.5 | 114.9 | 140.3 |
| 6 | 2 | 25 | 20.2 | 4.3 | 0.6 | 0.4 | 1.6 | 2.7 | 19.5 | 10.2 | 135.7 | 165.4 |
| 7 | 1 | 27 | 22.8 | 4.3 | 0.7 | 0.5 | 2.3 | 3.6 | 22.0 | 12.2 | 156.8 | 191.0 |
| 8 | 2 | 28 | 22.3 | 4.2 | 0.2 | 0.2 | 0.8 | 1.2 | 22.4 | 13.2 | 166.5 | 202.1 |
| 9 | 1 | 30 | 23.9 | 4.3 | 0.5 | 0.5 | 1.7 | 2.7 | 24.5 | 15.7 | 185.0 | 225.3 |
| 10 | 2 | 32 | 26.1 | 4.3 | 0.5 | 0.5 | 1.8 | 2.7 | 26.2 | 17.3 | 202.5 | 246.0 |
| 11 | 1 | 33 | 23.1 | 4.2 | 0.2 | 0.3 | 0.8 | 1.3 | 26.7 | 18.4 | 211.2 | 256.4 |
| 12 | 2 | 35 | 19.5 | 4.3 | 0.6 | 0.7 | 2.2 | 3.4 | 31.2 | 24.4 | 241.5 | 297.1 |
| 13 | 1 | 36 | 18.0 | 4.2 | 0.3 | 0.4 | 1.0 | 1.6 | 30.8 | 24.3 | 243.5 | 298.6 |
| 14 | 2 | 37 | 18.0 | 4.2 | 0.3 | 0.4 | 0.8 | 1.5 | 32.5 | 27.2 | 252.8 | 312.5 |
| 15 | 1 | 39 | 19.1 | 4.3 | 0.7 | 1.1 | 2.8 | 4.6 | 36.5 | 33.8 | 277.7 | 348.0 |
| 16 | 2 | 41 | 21.3 | 4.3 | 0.2 | 0.4 | 0.8 | 1.4 | 37.3 | 35.7 | 293.1 | 366.0 |
| 17 | 1 | 43 | 19.1 | 4.3 | 0.6 | 1.2 | 2.3 | 4.0 | 38.5 | 38.6 | 304.9 | 382.0 |
| 18 | 2 | 45 | 18.6 | 4.3 | 0.3 | 0.7 | 1.2 | 2.3 | 39.8 | 41.8 | 317.4 | 399.0 |
| 19 | 1 | 47 | 18.1 | 4.3 | 0.3 | 0.8 | 1.2 | 2.3 | 41.0 | 43.7 | 331.3 | 416.0 |
| 20 | 2 | 53 | 22.0 | 4.8 | 0.6 | 1.2 | 2.6 | 4.4 | 45.3 | 50.5 | 362.3 | 458.0 |

A: Column replacement
B: Used column
C: Culture time
D: Volume

DETAILED DESCRIPTION OF MAIN ELEMENTS

200: fermentation, separation, and refinement apparatus
180: first column 190: second column
112: adsorbent 114: filter
116: culture medium 118: stirrer
140: supply bath 150: storage bath
210: first conversion part 212: second conversion part
214: third conversion part 216: fourth conversion part
222: fifth conversion part 224: sixth conversion part
226: seventh conversion part

The invention claimed is:

1. A continuous fermentation, separation, and refinement method of products comprising:
   supplying a medium from a supply bath to a first column filled with a first adsorbent;
   culturing a microbe in the first column in which fermentation of the microbe occurs to produce the products;
   moving a culture medium containing the microbe and the medium in the first column to a second column when growth of the microbe in the first column is inhibited by an increase in concentration of the products or when productivity of the products of the microbe in the first column is decreased;
   stopping the supply of the medium to the first column, and switching a flow of the medium from the supply bath to the second column filled with a second adsorbent, in which culturing of the microbe continuously occurs; and
   desorbing the products from the first adsorbent of the first column to separate the products,
   wherein each of the first column and the second column has a filter preventing the first and the second adsorbents in each of the first and the second column from being eluted to be lost and a stirrer stirring the first and the second adsorbents and the products in each of the first and the second columns,
   the microbe is a microbe which can produce ethanol or butanol through microbial fermentation, the filter and the stirrer are inside the first and second columns, and the culture, the adsorption and the desorption are performed inside the columns.

2. The continuous fermentation, separation, and refinement method of claim 1, wherein the medium contains a raw material, and the raw material is fatty acid or sugars.

3. The continuous fermentation, separation, and refinement method of claim 1, wherein the products include alcohol, ketone, and carboxylic acid.

4. The continuous fermentation, separation, and refinement method of claim 1, wherein the culture medium circulates between the columns.

5. The continuous fermentation, separation, and refinement method of claim 1, wherein the desorption is performed using heat or an eluant.

6. The continuous fermentation, separation, and refinement method of claim 1, wherein the desorption is performed by applying heat to the adsorbed products in the first adsorbent to vaporize the products.

7. The continuous fermentation, separation, and refinement method of claim 1, wherein the desorption is performed using an eluant, which is an organic solvent, or an acidic or basic aqueous solution.

* * * * *